US008129107B2

(12) United States Patent
Fuhrmann et al.

(10) Patent No.: US 8,129,107 B2
(45) Date of Patent: Mar. 6, 2012

(54) BISULFITE CONVERSION OF DNA

(75) Inventors: Ina Fuhrmann, Berlin (DE); Matthias Ballhause, Berlin (DE)

(73) Assignee: Epigenomics AG, Berlin (DE)

( * ) Notice: Subject to any disclaimer, the term of this patent is extended or adjusted under 35 U.S.C. 154(b) by 427 days.

(21) Appl. No.: 11/887,609

(22) PCT Filed: Mar. 31, 2006

(86) PCT No.: PCT/EP2006/003193

§ 371 (c)(1),
(2), (4) Date: Apr. 23, 2009

(87) PCT Pub. No.: WO2006/103111

PCT Pub. Date: Oct. 5, 2006

(65) Prior Publication Data

US 2010/0041024 A1 Feb. 18, 2010

(30) Foreign Application Priority Data

Apr. 1, 2005 (EP) .................................... 05090090
May 12, 2005 (EP) .................................... 05090135

(51) Int. Cl.
*C12Q 1/68* (2006.01)
*B01L 3/00* (2006.01)
*C07H 21/00* (2006.01)

(52) U.S. Cl. ............................. 435/6; 422/61; 536/23.1

(58) Field of Classification Search ..... 435/6; 536/23.1; 422/61

See application file for complete search history.

(56) References Cited

FOREIGN PATENT DOCUMENTS

| | | |
|---|---|---|
| DE | 100 50 942 A1 | 4/2002 |
| WO | WO 2004/067545 A1 | 8/2004 |

*Primary Examiner* — Jezia Riley
(74) *Attorney, Agent, or Firm* — Kriegsman & Kriegsman

(57) ABSTRACT

The present invention relates to an improved method for the bisulfite conversion of DNA. In certain time-temperature ranges the efficacy of the bisulfite conversion is clearly improved. By combination with denaturating solvents, new reaction conditions and new purification methods the efficacy can be further increased The converted DNA can subsequently be analysed by different methods. The present invention facilitates the analysis of cytosine methylation.

37 Claims, 5 Drawing Sheets

BISULFITE CONVERSION OF DNA

BACKGROUND OF THE INVENTION

The present invention concerns a method for the detection of cytosine methylations in DNA. 5-Methylcytosine is the most frequent covalently modified base in the DNA of eukaryotic cells. For example, it plays a role in the regulation of transcription, in genetic imprinting and in tumorigenesis (for review: Millar et al.: Five not four: History and significance of the fifth base. In: S. Beck and A. Olek, eds.: The Epigenome. Wiley-VCH Verlag Weinheim, 2003, p. 3-20). The identification of 5-methylcytosine as a component of genetic information is thus of considerable interest. 5-Methylcytosine positions, however, cannot be identified by sequencing, since 5-methylcytosine has the same base-pairing behaviour as cytosine. In addition, in the case of a PCR amplification, the epigenetic information, which is borne by 5-methylcytosines, is completely lost.

The usual methods for methylation analysis operate essentially according to two different principles. Either methylation-specific restriction enzymes are utilized, or a selective chemical conversion of unmethylated cytosines to uracil is conducted (bisulfite treatment). The enzymatically or chemically pretreated DNA is then amplified and can be analyzed in different ways (for review: Fraga and Esteller: DNA Methylation: A Profile of Methods and Applications. Biotechniques 33: 632-649, September 2002; WO 02/072880, pp. 1 ff).

As the use of methylation-specific enzymes is restricted to certain sequences containing restriction sites recognised by said enzymes, for most applications a bisulfite treatment is conducted (for review: U.S. Ser. No. 10/311,661).

According to the invention a “bisulfite reaction”, “bisulfite treatment” or “bisulfite method” shall mean a reaction for the conversion of cytosine bases in a nucleic acid to uracil bases in the presence of bisulfite ions whereby 5-methyl-cytosine bases are not significantly converted. The bisulfite reaction contains a deamination step and a desulfonation step which can be conducted separately or simultaneously (further details are described and a reaction scheme is shown in EP 1394172 A1, incorporated by reference herein in its entirety). There are various documents addressing specific aspects of the bisulfite reaction, including Hayatsu et al., Biochemistry 9 (1970) 2858-28659; Slae and Shapiro, J. Org. Chem. 43 (1978) 4197-4200; Paulin et al., Nucl. Acids Res. 26 (1998) 5009-5010; Raizis et al., Anal. Biochem. 226 (1995), 161-1666; Wang et al. Nucleic Acids Res. 8 (1980) 4777-4790. These documents are summarized in EP 1394172 A1 (incorporated by reference herein in its entirety).

The bisulfite treatment is usually conducted in the following way: The genomic DNA is isolated, mechanically or enzymatically fragmentised, denaturated by NaOH, converted several hours by a concentrated bisulfite solution and finally desulfonated and desalted (e.g.: Frommer et al.: A genomic sequencing protocol that yields a positive display of 5-methylcytosine residues in individual DNA strands. Proc Natl. Acad. Sci. USA 1992 Mar. 1; 89(5):1827-31; incorporated by reference herein in its entirety).

In recent times several technical improvements of the bisulfite methods were developed. The agarose bead method incorporates the DNA to be investigated in an agarose matrix, through which diffusion and renaturation of the DNA is prevented (bisulfite reacts only on single-stranded DNA) and all precipitation and purification steps are replaced by rapid dialysis (Olek A. et al. A modified and improved method for bisulphite based cytosine methylation analysis, Nucl. Acids Res. 1996, 24, 5064-5066). In the patent application WO 01/98528 (=DE 100 29 915; =U.S. application Ser. No. 10/311,661) a bisulfite conversion is described in which the DNA sample is incubated with a bisulfite solution of a concentration range between 0.1 mol/l to 6 mol/l in presence of a denaturating reagent and/or solvent and at least one scavenger. In said patent application several suitable denaturating reagents and scavengers are described (document incorporated by reference herein in its entirety). In the patent application WO 03/038121 (=DE 101 54 317; =U.S. Ser. No. 10/416,624) a method is disclosed in which the DNA to be analysed is bound to a solid surface during the bisulfite treatment. Consequently, purification and washing steps are facilitated. Further improvements are described in the patent applications EP 1394173 A1 and EP 1394172 A1 (incorporated by reference herein in its entirety). The patent application PCT/EP2004/011715 (=DE 103 47 396.3; DE 103 47 397.1; DE 103 47 400.5; DE 103 47 399.8) describes an improved bisulfite treatment by using dioxane or n-alkylene glycol compounds in combination with a special temperature program and a special purification step by ultrafiltration. In said patent application a reaction temperature of 50° C. for 5 h is described (Example 2).

However, a basic problem of the bisulfite treatment consists of the fact that long reaction times are necessary in order to assure a complete conversion and to exclude false-positive results. Simultaneously, however, this leads to a degradation of the DNA due to the long reaction times. Higher reaction temperatures in fact lead to a higher conversion rate, but also to a more intense degradation of the DNA. The interactions between temperature, reaction time, rates of conversion and degradation were recently investigated systematically. In this way, it could be shown that the highest conversion rates were attained at temperatures of 55° C. (with reaction times between 4 and 18 hours) and at 95° C. (with a reaction time of one hour). A serious problem, however, is the degradation of the DNA during this procedure. It is described that at a reaction temperature of 55° C., 84-96% of DNA is decomposed. At 95° C. the degradation is even higher (Grunau et al.: Bisulfite genomic sequencing: systematic investigation of critical experimental parameters. Nucleic Acids Res. 2001 Jul. 1; 29(13):E65-5; incorporated by reference herein in its entirety). Thus, most authors use reaction temperatures of approximately 50° C. (see: Frommer et al., loc. cit. 1992, p. 1827; Olek et al., loc. cit. 1996, p. 5065; Raizis et al: A bisulfite method of 5-methylcytosine mapping that minimizes template degradation. Anal Biochem. 1995 Mar. 20; 226(1):161-6, 162). In the patent application WO 2004/067545 A1 (applicant: Hoffmann-La Roche) an improved bisulfite treatment is disclosed using a reaction temperature between 70 and 90° C. for 1.5 to 3.5 hours.

Due to the high losses of the conventional bisulfite treatment, it is problematic to use these methods for investigations in which the quantity of DNA to be analyzed is limited. A particularly interesting field of methylation analysis, however, lies in diagnosing cancer diseases or other disorders associated with a change in methylation status by means of analysis of DNA from bodily fluids, e.g. from blood or urine. However, DNA is present only in small concentrations in body fluids, so that the applicability of methylation analysis is limited by the low yield of conventional bisulfite treatment.

Accordingly, based on the particular importance of cytosine methylation analysis and based on the described disadvantages of conventional methodology, there is a great technical need for improved methods of bisulfite conversion.

It was now found that under certain optimized reaction conditions using denaturating reagents, a reaction temperature >50° C., particularly >55° C., and a reaction time ≧5 h the conversion rate of the bisulfite reaction is increased in an unexpected, surprising way. This could be shown by a new method enabling an exact determination of the conversion rate of the DNA (see EP 05 075 404.3, incorporated by reference in its entirety). In a preferred embodiment of the invention certain time-temperature combinations are used (60° C./5 h and 55° C./7 h). Usually the bisulfite conversion using denaturating reagents is conducted at 50° C. for 5 h (see example 2 in PCT/EP2004/011715).

Although it is known to the person skilled in the art that increases in temperature or time can increase the performance of reaction, the person skilled in the art could not expect that the herein disclosed time-temperature rise would cause such a strong effect, particularly because it was thought that an time/temperature increase would lead to a higher degradation of the DNA (see above). The new method, however, leads to a higher amount of converted, aplificable DNA. The new method is particularly applicable for the analysis of DNA derived from bodily fluids, e.g. blood or plasma. In combination with additives, improved reaction conditions and/or new purification methods the efficacy of the conversion can be further improved. Thereby a sensitive DNA methylation analysis of bodily fluids becomes possible.

A further aspect of the present invention relates to the use of particular radical scavengers in the bisulfite reaction.

The use of radical scavengers for the bisulfite reaction is already known (DE 10029915), but most of the known methods use hydroquinone as a radical scavenger (see: Fromer et al: A genomic sequencing protocol that yields a positive display of 5-methylcytosine residues in individual DNA strands. Proc. Natl. Acad. Sci. USA, 1992 Mar. 1; 89 (5):1827-31).

DESCRIPTION

Unexpected it was found, that it is possible to increase the yield of the bisulfite reaction, if specific radical scavengers, especially chroman acid derivatives or gallic acid derivatives, were added to the reaction mixture. According to the present invention vitamin E derivatives, especially chroman derivates are inserted. These compounds lead to a significant increase of the conversion rate compared to hydroquinone. The use of certain chroman derivatives is already known (PCT/EP2004/011715), but these radical scavengers are only used in combination with denaturating solvents.

Now it was found, that it is possible to increase the conversion rate of bisulfite reaction by adding chroman derivatives in absence of denaturating solvents. If it is possible to perform the bisulfite reaction without addition of denaturating solvents, this leads to various advantages, for example to a simplification of the purification of the DNA.

The efficiency of the conversion can significantly be improved through the combination of the use of radical scavengers with special temperature profiles and new purification methods. A sensitive methylationanalysis of isolated DNA from tissue or from body fluids is possible.

One aspect of the invention described herein is a method for bisulfite conversion of DNA, wherein the bisulfite reaction is conducted at a temperature >50° C. and with a reaction time ≧5 h.

In a preferred embodiment the bisulfite reaction is conducted at a temperature >55° C.

The bisulfite reaction is conducted with an optimum reaction time between 5 h and 18 h.

In a further preferred embodiment the bisulfite reaction is conducted within a temperature range from 57° C. to 65° C. and a time range form 4 h and 30 min to 5 h and 30 min or within a temperature range from 52° C. to 57° C. and a time range from 6 h and 30 min to 7 h and 30 min.

In a preferred embodiment the conversion is carried out within a temperature range from 57° C. to 65° C. and a time range from 4 h and 45 min to 5 h and 15 min or within a temperature range from 52° C. to 57° C. and a time range from 6 h and 45 min to 7 h and 45 min.

In a further preferred embodiment the conversion is carried out within a temperature range from 59° C. to 62° C. and a time range from 4 h and 45 min to 5 h and 15 min or within a temperature range from 54° C. to 56° C. and a time range from 6 h and 45 min to 7 h and 45 min.

In a particular preferred embodiment the conversion is conducted a temperature of 60° C. for 5 h or at a temperature of 55° C. for 7 h.

Another aspect of the present invention relates to the use of particular radical scavengers in the bisulfite treatment.

According to the method of the present invention the bisulfite conversion is conducted in the presents of a radical scavenger. Preferred radical scavengers are vitamin E or a vitamin E derivatives, more preferred chroman or a chroman derivative, especially 6-hydroxy-2,5,7,8-tetramethylchroman-2-carboxylic acid (Trolox™).

Preferred radical scavengers have the following general formula:

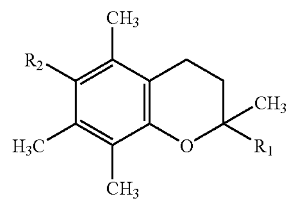

with $R_1$=H, COOH, $[CH_2CH_2CH_2(CH_3)]_3$—$CH_3$
with $R_2$=H, OH, OAc

More preferred radical scavengers with the following formula are inserted:

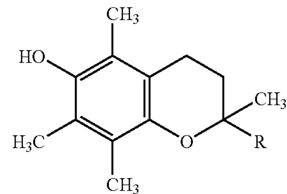

with R=H, COOH, $[CH_2CH_2CH_2(CH_3)]_3$—$CH_3$

Especially more preferred compounds with the following formula are inserted:

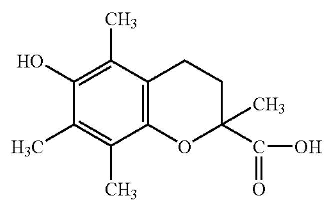

Which is 6-hydroxy-2,5,7,8-tetramethylchroman-2-carboxylic acid (Trolox™).

In a preferred embodiment compounds of the following formula are used:

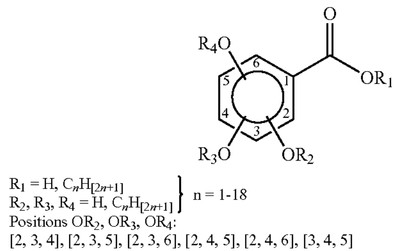

In another preferred embodiment trihydroxybenzoic acid and derivates thereof, in particular gallic acid (3,4,5-trihydroxy benzoic acid) and derivatives of gallic acids are employed as scavengers in the bisulfite conversion.

In acidic solutions gallic acid is more efficient than standard radical-scavengers. Gallic acid has also the advantage of being soluble in water which might avoid complications during the purification.

The radical scavenger properties are caused through the aromatic ring system. Therefore it is expectable, that changes in the side chain have no significant influence on the radical scavenger properties. Due to clarity reasons only preferred compounds are presented in here which are especially suitable for the present invention, because of their solubility properties, and which are commercially easy available.

The radical scavengers of the present invention are inserted in a concentration range (referred to the reaction solvent) from 1 to 500 mmol/l, more preferred in a concentration range from 10 to 100 mmol/l an especially in a concentration range from 20 to 60 mmol/l.

In a preferred embodiment of the invention the concentration for Trolox™ is between 35 and 50 mmol/l and for gallic acid and gallic acid derivatives between 50 and 60 mmol/l.

It could be advantageous for the performance of the reaction to insert a solvent to the reaction mixture which increases to solubility of the radical scavenger. Suitable solvents are for example non denaturating alcohols, aldehydes or keton compounds.

The DNA to be investigated may originate from different sources depending on the diagnostic or scientific objective. For diagnostic investigations, tissue samples may be used as the initial material. Due to the increased sensitivity of the bisulfite conversion, it is preferred to analyse bodily fluids, particularly serum or plasma. It is also possible to use DNA from sputum, stool, urine, or cerebrospinal fluid. The DNA is extracted according to standard methods, from blood, e.g., with the use of the Qiagen UltraSens® DNA extraction kit. Other methods for purifying DNA are known to the person skilled in the art.

Subsequently, the isolated DNA may be fragmented, e.g., by reaction with restriction enzymes. The reaction conditions and the enzymes employed are known to the person skilled in the art and are taken, e.g., from the protocols supplied by the manufacturers.

The bisulfite conversion may be conducted under standard reaction conditions. However, the reaction can be conducted in the presence of certain denaturating additives (PCT/EP2004/011715). Thus, the reaction could be carried out in the presence of a compound out of the group of dioxane, one of its derivatives and a similar aliphatic cyclic ether.

It is also particularly preferred that the reaction is carried out in the presence of a compound of the following formula:

$$R_1O-\left[\left[CH_2\right]_m-CH_2-O\right]_n-R_2$$

n=1-35000 m=1-3

$R_1$=H, Me, Et, Pr, Bu $R_2$=H, Me, Et, Pr, Bu

Preferred are thus n-alkylene glycol compounds, particularly their dialkyl ethers, and especially diethylene glycol dimethyl ether (DME) (see PCT/EP2004/011715).

The bisulfite conversion may be produced according to the known, protocols indicated above. The reaction may take place both in solution as well as also on DNA bound to a solid phase. Sodium disulfite (=sodium bisulfite/sodium metabisulfite) is used, since it is more soluble in water than sodium sulfite. The disulfite salt disproportionates in aqueous solution to the hydrogen sulfite anions necessary for the cytosine conversion. When bisulfite concentration is discussed below, this refers to the concentration of hydrogen sulfite and sulfite anions in the reaction solution. For the method according to the invention, concentration ranges of 0.1 to 6 mol/l are possible (see above). The concentration range should be between 1 to 6 mol/l or better between 2 to 4 mol/l. However, when dioxane is used, the maximal concentration of bisulfite that can be used is smaller (see below). In selecting the bisulfite concentration, one must consider that a high concentration of bisulfite leads to a high conversion, but also leads to a high decomposition rate due to the lower pH.

Dioxane can be utilized in different concentrations. The dioxane concentration amounts to 10 to 35% (vol/vol), or better between 20 to 30% or best between 22 to 28%, especially 25%. A dioxane concentration higher than 35% is problematic, since this results in a formation of two phases within the reaction solution. In embodiments with a dioxane concentration of 22 to 28%, the final preferred bisulfite concentration amounts to 3.3 to 3.6 mol/l, and in another better embodiment with a dioxane concentration of 25%, it amounts to 3.5 mol/l (see PCT/EP2004/011715).

The n-alkylene glycol compounds according to the invention can be utilized in a different concentration range. DME is used in concentrations between 1 to 35% (vol/vol). The optimum is between 5 and 25%, and best is 10% DME (see PCT/EP2004/011715).

The preferred scavengers utilised according to the invention are chromane derivatives, e.g., 6-hydroxy-2,5,7,8-tetramethylchroman-2-carboxylic acid (also known as: Trolox™ C) or gallic acid derivates (see above). However, for the inventive time-temperature windows, different scavengers might be used. Further scavengers are listed in the patent application WO 01/98528 (=DE 100 29 915; =U.S. application Ser. No. 10/311,661; incorporated herein in its entirety).

In the method according to the present invention, the reaction temperature is clearly increased for a short time at least once during the course of the conversion. In this way, the effectiveness of the bisulfite conversion can be further increased (see PCT/EP2004/011715). The temperature increases of short duration are named "thermospikes" below. The reaction temperature during a thermospike is increased to over 85° C. by at least one thermospike. The optimal number of thermospikes is a function of the basic reaction temperature. The higher the optimal number of thermospikes is, the lower is the basic reaction temperature. At least one thermospike is necessary in each case. And, on the other hand, in principle, any number of thermospikes is conceivable. Of course, it must be considered that with a large number of temperature increases, the decomposition rate of the DNA also increases, and an optimal conversion is no longer assured. The optimum number of thermospikes is thus between 1 and 10 thermospikes each time, depending on the basic reaction temperature. A number of two to 5 thermospikes is thus the optimum. The thermospikes increase the reaction temperature preferably to 85 to 100° C., particularly preferably to 90 to 98° C., and most preferably to 94° C. to 96° C.

The duration in time of the thermospikes also depends on the volume of the reaction batch. It must be assured that the temperature is increased uniformly throughout the total reaction solution. For a 20 µl reaction batch when using a thermocycler a duration between 15 seconds and 1.5 minutes, especially a duration between 20 and 50 seconds leads to good results and a duration of 30 seconds is the optimum. Operating on a volume of 100 µl the range lies between 30 seconds and 5 minutes, especially between 1 and 3 minutes. The optimum range is 1.5 minutes. For a volume of 600 µl, a duration of 1 to 6 minutes, especially between 2 and 4 minutes and best 3 minutes. A person skilled in the art will easily be able to determine suitable durations of thermospikes in relation to a variety of reaction volumes.

After the bisulfite conversion is completed, the DNA is desulfonated and purified. Different methods are known for this purpose (e.g., see: DE 101 54 317 A1=U.S. Ser. No. 10/416,624; Grunau et al. 2001, loc. cit.). Normally, the reaction solution is first treated with sodium hydroxide. Subsequently a neutralization and alcohol precipitation of the DNA are carried out. In one embodiment of the above-described embodiments according to the invention, the purification is performed by means of a gel filtration, e.g., with Sephadex-G25 columns (see PCT/EP2004/011715). The bisulfite salt can be removed very effectively in this way, without the need for further washing steps. In another embodiment, the purification is conducted via DNA-binding surfaces, e.g., via the Wizard DNA purification resin of Promega (see: Kawakami et al., loc. cit.). A third embodiment utilizes magnetic particles for purification, e.g., with the help of the Magna-Pure® process. These purification methods lead to particularly good results in combination with the n-alkylene glycol compounds according to the invention, particularly with DME. The purification is conducted according to the manufacturer's instructions. It is known to the person skilled in the art that an even further increased yield may be attainable by variation of the manufacturer's instructions by using standard experiments. Correspondingly, optimized protocols are also part of this invention. Further technical instructions for purifying nucleic acids via gel filtration, DNA-binding surfaces and magnetic particles are known to the person skilled in the art and are provided, e.g., from the manufacturer's instructions. In a most particularly preferred embodiment, purification is conducted by means of an ultrafiltration. Such a procedure has several technical advantages and results in a surprisingly successful purification of the converted DNA (see PCT/EP2004/011715). Different commercially available ultrafiltration systems are known to the person skilled in the art, which may be used for the method according to the invention. In another embodiment, Microcon™ columns of Millipore are used. The purification can thus be carried out according to a modified manufacturer's protocol. For this purpose, the bisulfite reaction solution is mixed with water and loaded onto the ultrafiltration membrane. Subsequently the reaction solution is centrifuged for about 15 minutes and then washed with 1×TE buffer. The DNA remains on the membrane in this treatment. Next, desulfonation is performed. For this purpose, 0.2 mol/l NaOH is added and the DNA incubated for 10 min. Another centrifugation (10 min) is then conducted, followed by a washing step with 1×TE buffer. The DNA is subsequently eluted. For this purpose, the membrane is mixed with 50 µl of warm 1×TE buffer (50° C.) for 10 minutes. The membrane is turned over according to the manufacturer's instructions and a repeated centrifugation is conducted, by means of which the DNA is removed from the membrane. Now the eluate can be used directly for the intended detection reactions. It is known to the person skilled in the art that other procedures may be indicated with other ultrafiltration systems, and that a good yield can also be obtained by varying the above-indicated conditions. The corresponding embodiments are also part of this invention.

The DNA which has been converted and purified via the above-described different embodiments may now be analysed in different ways. It is particularly preferred to amplify the DNA first by means of a polymerase chain reaction. Thus, a selective amplification of the originally methylated or unmethylated DNA can be assured via different methods, e.g., via the so-called "HeavyMethyl" method (for review: Cottrell et al.; A real-time PCR assay for DNA-methylation using methylation-specific blockers. Nucleic Acids Res. 2004 Jan. 13; 32(1):e10. WO 02/072880) or the so-called "methylation-sensitive PCR" ("MSP"; see: Herman et al.: Methylation-specific PCR: a novel PCR assay for methylation status of CpG islands. Proc Natl Acad Sci USA. 1996 Sep. 3; 93(18): 9821-6). The amplificates obtained may be detected via conventional methods, e.g., via primer extension reactions ("MsSNuPE"; see, e.g.; DE 100 10 280=U.S. Ser. No. 10/220,090) or via hybridization to oligomer arrays (see e.g.: Adorjan et al., Tumour class prediction and discovery by microarray-based DNA methylation analysis. Nucleic Acids Res. 2002 Mar. 1; 30(5):e21). In another particularly preferred embodiment, the amplificates are analysed with the use of PCR Real Time variants (see: U.S. Pat. No. 6,331,393 "Methyl Light"). Preferred variants are therefore the "Taqman" and the "Lightcycler" methods.

The methods disclosed here are preferably used for the diagnosis and/or prognosis of adverse events for patients or individuals, whereby these adverse events belong to at least one of the following categories: undesired drug interactions; cancer diseases; CNS malfunctions, damage or disease; symptoms of aggression or behavioral disturbances; clinical and psychological consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as an abnormality in the development process; malfunction, damage or disease of the skin, of the muscles, of the connective tissue or of the bones; endocrine and metabolic malfunction, damage or disease; headaches or sexual malfunction.

The new method also serves in a particularly preferred manner for distinguishing cell types, tissues or for investigating cell differentiation.

The new method also serves in a particularly preferred manner for analysing the response of a patient to a drug treatment.

Also the preferred use of the above-described radical scavengers for the bisulfite conversion of DNA is part of the present invention. Preferred is the use of vitamin E or vitamin E derivatives, more preferred chroman or chroman derivatives and especially preferred 6-hydroxy-2,5,7,8-tetramethylchroman-2-carboxylic acid (Trolox™).

Further preferred is the use of trihydroxybenzoic acid and trihydroxybenzoic acid derivatives, especially gallic acid and gallic acid derivatives.

Preferred is the use of chroman derivatives for the bisulfite reaction in absence of denaturating solvents/reagents.

Also preferred is the us of compounds according to the above mentioned formulas.

Preferred is the use of radical scavengers having a concentration from 1 to 500 mmol/l, more preferred having a concentration form 10 to 100 mmol/l and especially preferred having a concentration from 20 to 60 mmol/l.

In a preferred embodiment of the invention the concentration of chroman derivatives is 35 to 50 mmol/l and for trihydroxybenzoic acid derivatives 30 to 60 mmol/l.

A kit according to the present invention contains a bisulfite reagent and a radical scavenger. Further compounds of the kit could be a microfiltration tubes, primer, polymerase and compounds necessary for the bisulfite conversion, purification and/or amplification.

The kit should not contain a denaturating solvent/reagent. Preferred the radical scavenger is a vitamin E derivative, especially a chroman derivative like 6-hydroxy-2,5,7,8-tetramethylchroman-2-carbonsäure (Trolox™), respectively trihydroxybenzoic acid derivatives.

EXAMPLES

Example 1

It will be shown that the optimized bisulfite method makes possible a sensitive methylation analysis obtained of DNA from body fluids. For this purpose, 1 ml of human plasma was mixed with a specific quantity of human DNA. The DNA was isolated from the plasma samples via the Magna Pure method (Roche) according to the manufacturer's instructions. The 100 μl of eluate resulting from the purification were utilized completely in the following bisulfite reaction. The procedure for the method according to the invention was as follows: The eluate was mixed is with 354 μl of bisulfite solution (5.89 mol/l) and 146 μl of dioxane containing a radical scavenger (6-hydroxy-2,5,7,8-tetramethylchroman-2-carboxylic acid, 98.6 mg in 2.5 ml of dioxane). The reaction mixture was denaturated for 3 min at 99° C. and subsequently incubated with one of the following temperature/time programs:

a) for a total of 5 h: 30 min 50° C.; one thermospike (99.9° C.) for 3 min; 1.5 h 50° C.; one thermospike (99.9° C.) for 3 min; 3 h 50° C.;
b) for a total of 5 h: 30 min 60° C.; one thermospike (99.9° C.) for 3 min; 1.5 h 60° C.; one thermospike (99.9° C.) for 3 min; 3 h 60° C.; or
c) for a total of 7 h: 30 min 55° C.; one thermospike (99.9° C.) for 3 min; 1.5 h 55° C.; one thermospike (99.9° C.) for 3 min; 5 h 55° C.

All reaction mixtures were subsequently purified by ultrafiltration by means of a Millipore Microcon™ column. The purification was conducted essentially according to the manufacturer's instructions. For this purpose, the reaction mixture was mixed with 300 μl of water, loaded onto the ultrafiltration membrane, centrifuged for 15 min and subsequently washed with 1×TE buffer. The DNA remains on the membrane in this treatment. Then desulfonation is performed. For this purpose, 0.2 mol/l NaOH was added and incubated for 10 min. A centrifugation (10 min) was then conducted, followed by a washing step with 1×TE buffer. After this, the DNA was eluted. For this purpose, the membrane was mixed for 10 minutes with 50 μl of warm 1×TE buffer (50° C.). The membrane was turned over according to the manufacturer's instructions. Subsequently a repeated centrifugation was conducted, with which the DNA was removed from the membrane. 10 μl of the eluate were utilized for the following Lightcycler Real Time PCR.

A fragment of the human GSTPi-Gene was analysed. The following primer and probes were used: Forward primer: GGAGTGGAGGAAAtTGAGAt (Seq. ID 1); reverse primer: CCTAATCAACACACAATCACTAA (Seq. ID 2); Taqman probe: FAM-TGGGTGTTTGTAATTTTTGTTTTGTGTTAGGTT-TAMRA (Seq. ID 3).

The amplification was conducted by means of a bisulfite-specific assay. The fluorescent signals were detected and the amount of converted and isolated DNA was quantified by a comparison with calibration curves. FIG. 1 shows the results of the experiment. An increase in temperature to more than 50° C. and an increase in the reaction time to more than 5 h leads to a significantly increased yield in DNA conversion. The new method therefore leads to a substantially higher amount of converted, amplificable DNA. This applies particularly to the time/temperature combinations of 5 h/60° C. and 7 h/55° C. The detected DNA concentration in the improved method is more than twice the DNA-concentration of the 5 h/50° C. combination. This result is surprising, as a person skilled in the art would not have expected such a difference in the performance of the reaction conditions.

Further results are shown in FIG. 2.

Example 2

In an experiment similar to Example 1 bisulfite conversions in different time-temperature windows were conducted: (3.0 h/50° C. and 5.0 h/60° C.). 5 ng mDNA (Chemicon) in a background of 1μ PBL-DNA (Promega) were analysed. The converted DNA was purified as described above. The converted DNA was amplified by the "HM" technology using methylation specific oligonucleotide blockers. The real time PCR curves are shown in FIG. 3. The temperature/time combination of 5 h/60° C. clearly leads to the best result.

Example 3

Due to the compounds of the present invention it is possible to increase the conversion rate of the bisulfite reaction in comparison to the use of conventionally hydroquinone. Thereto the serum DNA was isolated by using the MagNaPure method (Roche) according to the manufacture indications. Afterwards the extracts of several samples are pooled. Always 500 μl of a bisulfite solution (4.17 mol/l) have been added to 100 μl. 6-hydroxy-2,5,7,8-tetramethylchroman-2-carboxylic acid respectively hydroquinone was inserted as a radical scavenger. The reaction mixture was denaturated for 3 min at 99° C. and afterwards incubated for 5 h at the following temperature program: 30 min at 50° C.; one thermospike (99.9° C.) for 3 min; 1.5 h at 50° C.; one thermospike (99.9° C.) for 3 min; 3 h at 50° C. Afterwards the reaction mixture of the control as well as the one of the method according to the present invention were purified per ultrafiltration by means of a millipore micron column. The purification was substantially performed according to the manufacture's instructions. For this purpose 300 μl water were added to the reaction mixture and afterwards placed on the ultrafiltration membrane, centrifugated of 15 min and then washed with 1×TE-buffer. During this treatment the DNA stays on the membrane. Afterwards the desulphonation follows. For this purpose 0.2 mol/l NaOH were added and incubated for 10 min. Afterwards a centrifugation (10 min) and a washing step with 1×TE-buffer follows. Hereafter the DNA was eluted. For this purpose 50 μl warm 1×TE-buffer (50° C.) was added for 10 to the membrane. The membrane was used according to the manufacture's instructions. Afterwards the DNA, which was removed from the membrane, was again centrifuged. 10 μl eluate were used for the following Lightcycler real time PCR. Hereby the amplification was performed by means of bisulfite specific assays. 6 replicas were made per variation. The fluorescence signals were detected and calculated with the Lightcycler software. The fluorescence curves of the amplifications are shown in FIG. 1. It is shown significantly, that the amplification is significantly better detectable when adding 6-hydroxy-2,5,7,8-tetramethylchroman-2-carboxylic acid then when adding hydroquinone. Furthermore the detected signals of the method of the present invention are significant stronger. Therefore the conversion rate of the bisulfite conversion is significantly increased.

Example 4

Gallic acid (3,4,5-trihydroxy benzoic acid, Acros, M 170.12 g/mol) was used as a scavenger in the bisulfite conversion, compared to Trolox™. In acidic solutions gallic acid is even more efficient than the standard radical-scavenger Trolox™ C (6-hydroxy-2,5,7,8 tetramethylchroman-2-carboxylic acid). Gallic acid has also the advantage of being soluble in water which might avoid complications during the purification.

A stock-solution was prepared by dissolving 85.2 mg gallic acid in dioxane. The efficiency of the radical-scavenger was tested by diluting the stock to lower concentrations:

| Gallic Acid [mg] | Radical-Scavenger Stock [μl] | Dioxane [μl] | Final Concentration [mmol] |
|---|---|---|---|
| 85.1 | -:- | 2500 | 50 |
| [68.1] | 116.8 | 29.2 | 40 |
| [51.1] | 87.6 | 58.4 | 30 |

Trolox™ was used in final concentrations of 33 mmol/l.

A DNA-mastermix was prepared containing 95 ng undigested PBL-DNA (Promega) and 5 ng methylated DNA (Chemicon) in 100 μl input-volume. Methylated DNA was used to analyse samples with the very sensitive HeavyMethyl-assay 15667.6. For each tested concentration 6 replicates were bisulfite-treated. For a better comparison six additional samples were treated. The bisulfite treatment was conducted as described in Example 3.

As a result, it could be shown that gallic acid had very good physical properties for the application in the bisulfite conversion. It dissolves without problems in dioxane and no problems occur during the purification.

Gallic acid seems to be a very efficient radical scavenger. In a preferred embodiment, a concentration of 50 mmol concentration in the bisulfite reaction is employed. The results of the bisulfite treatment using gallic acid compared to Trolox™ are shown in FIG. 5. The application of gallic acid leads to an improved conversion.

The gallic acid offers excellent physical properties for preparation of bisulfite-reaction-mixtures and do not interfere with the purification over Microcon-columns. The compound has also excellent chemical properties and can be used as radical scavenger within the bisulfite-reaction.

SEQUENCE LISTING

Figure 1:
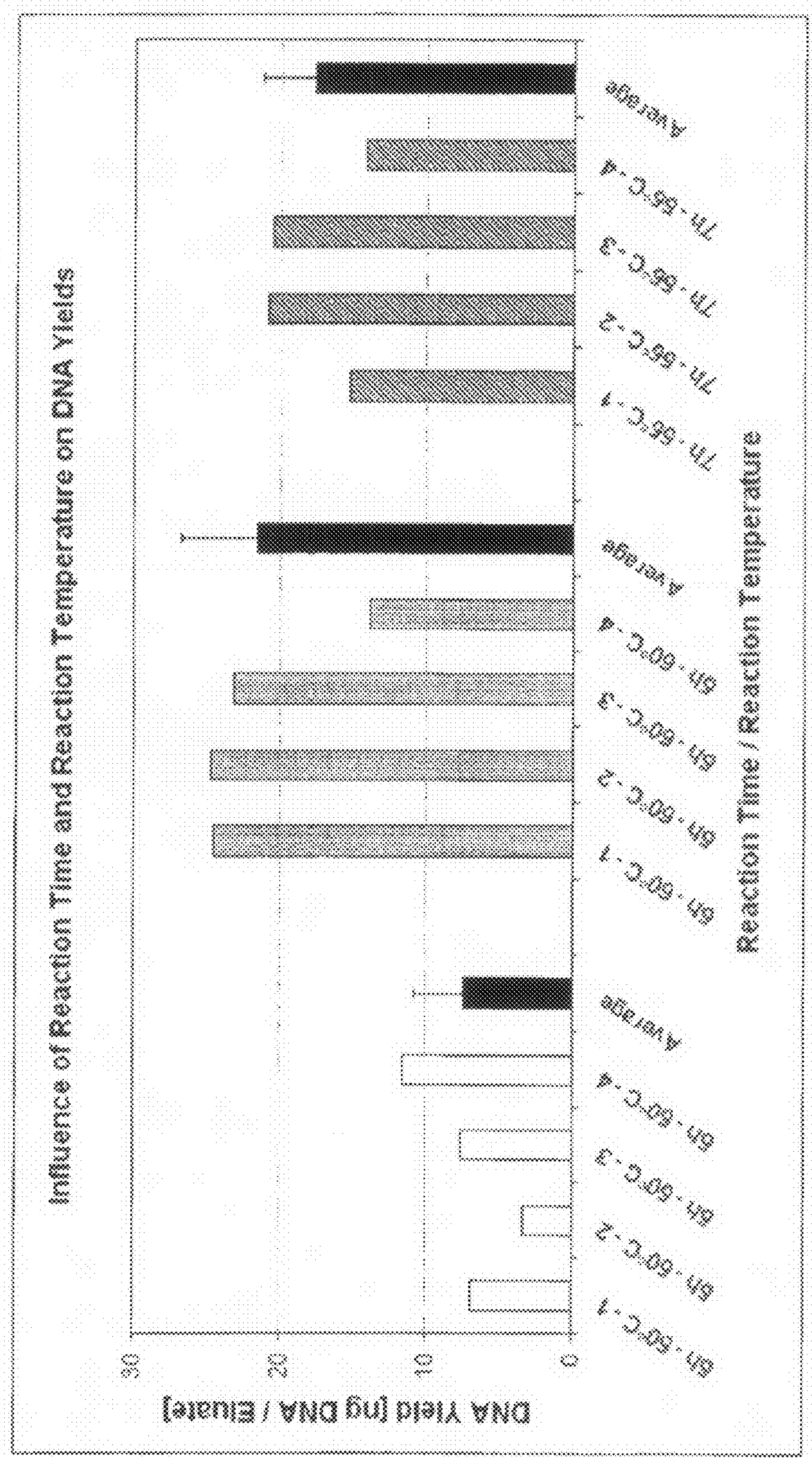
FIG. 1 shows the results of Example 1. DNA was isolated from plasma samples, treated with bisulfite under different time/temperature combination and amplified by means of a Lightcycler PCR. The DNA yield in the combinations 5 h/60° C. and 7 h/55° C. is much higher than in the combination 5 h/50° C.
Figure 2:
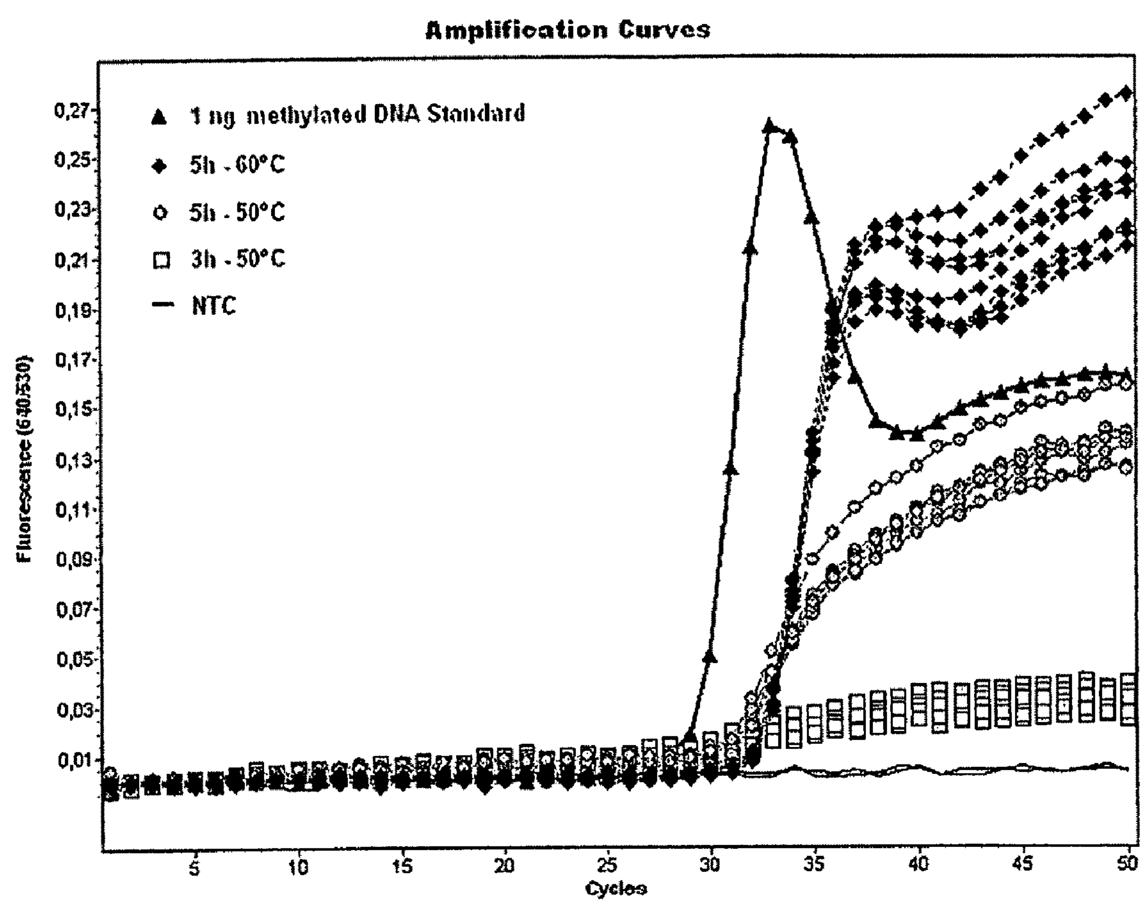
FIG. 2 shows further results of Example 1
Figure 3:
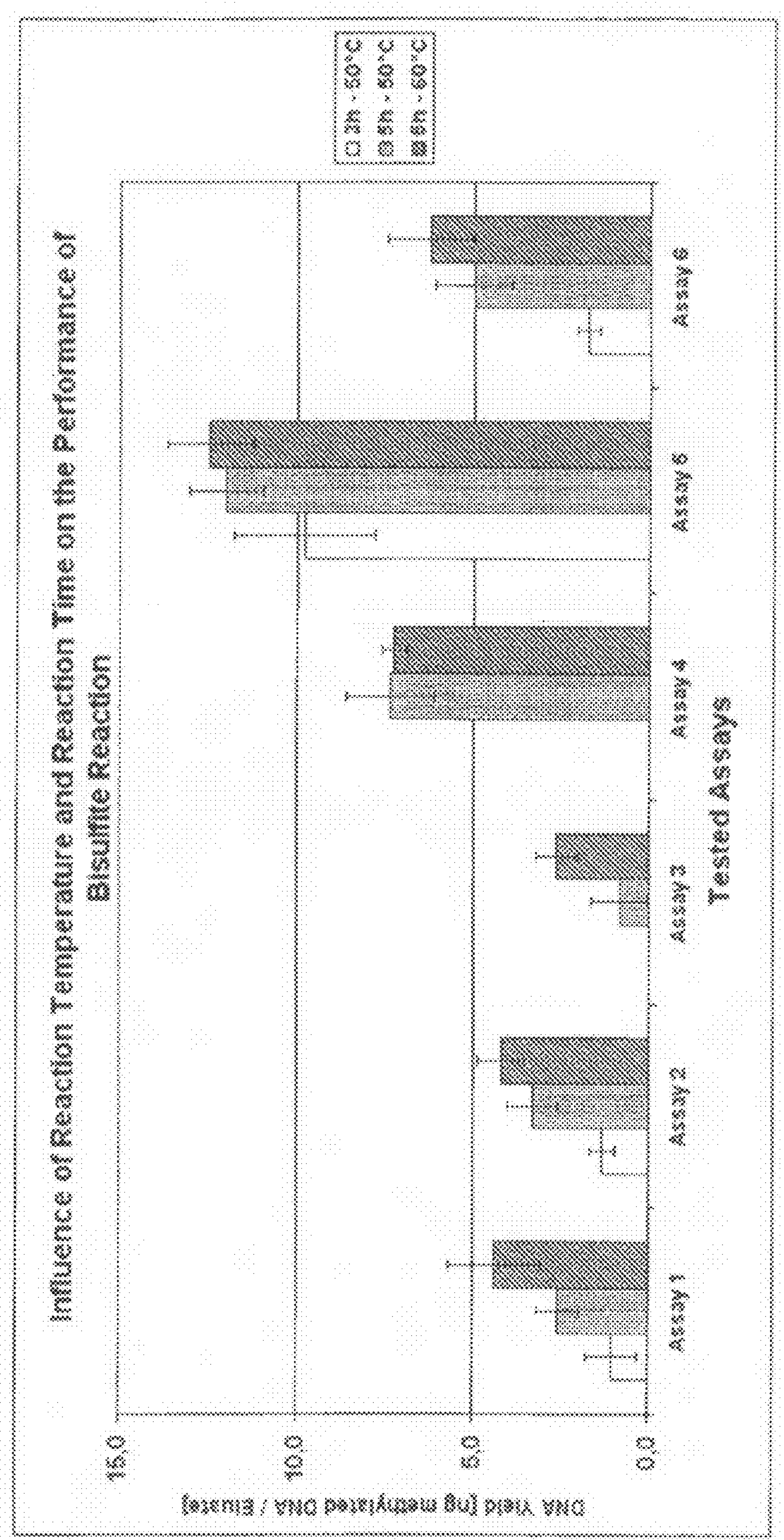
FIG. 3 shows the results of Example 2. Presented are the real time PCR curves of DNA converted in different time/temperature windows. Subsequently, the DNA was amplified using methylation specific blockers.
Figure 4:
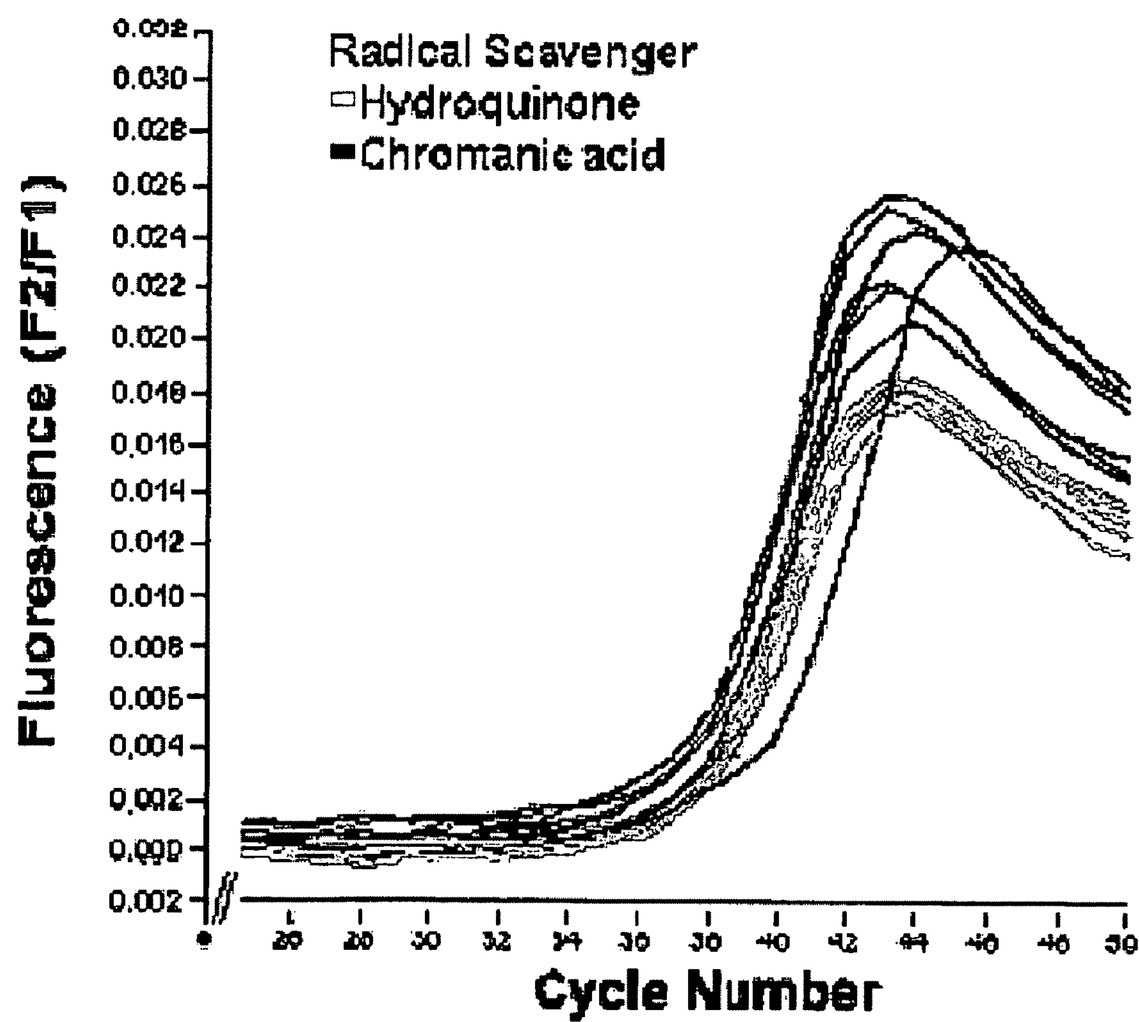
FIG. 4 shows the results of Example 3. DNA was bisulfite treated in the presence of a scavenger (either hydrochinone or Trolox™) and subsequently analysed via real time PCR.
Figure 5:
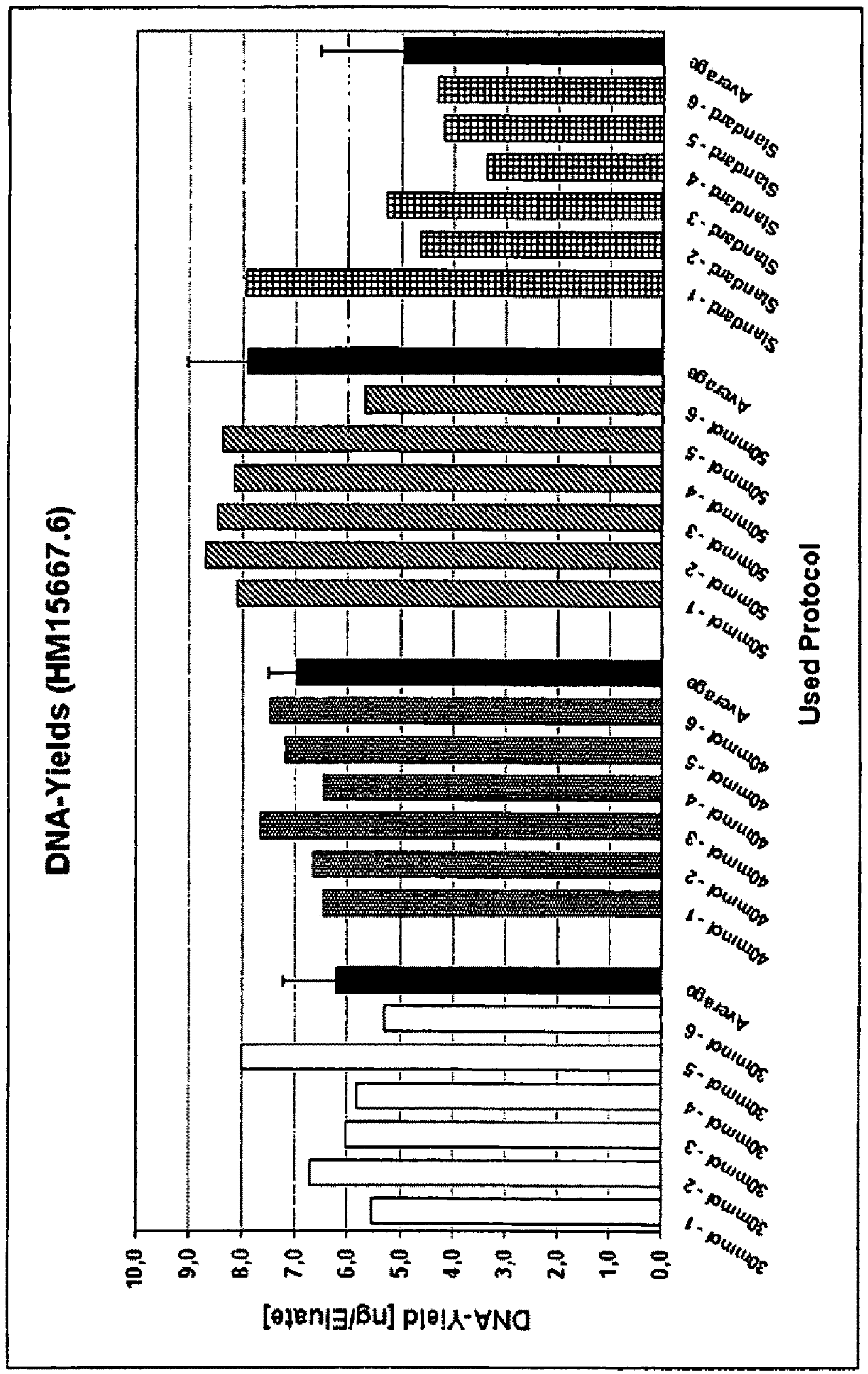
FIG. 5 shows the results of example 4. The performance of different concentrations of gallic acid as a scavenger was compared to a standard (Trolox™ with final concentration of 33 mmol/l). It could be shown that gallic acid even leads to a higher yield than Trolox™).

```
<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1

ggagtggagg aaattgagat                                                20


<210> SEQ ID NO 2
<211> LENGTH: 23
<212> TYPE: DNA
<213> ORGANISM: Artificial Sequence
<220> FEATURE:
<223> OTHER INFORMATION: reverse primer

<400> SEQUENCE: 2
```

-continued

```
cctaatcaac acacaatcac taa                                          23


<210> SEQ ID NO 3
<211> LENGTH: 33
<212> TYPE: DNA
<213> ORGANISM: Artificial Sequence
<220> FEATURE:
<223> OTHER INFORMATION: taqman probe

<400> SEQUENCE: 3

tgggtgtttg taatttttgt tttgtgttag gtt                               33
```

The invention claimed is:

1. Use of a compound for the bisulfite conversion of DNA, said use comprising converting isolated genomic DNA in the presence of the compound, wherein the compound has the following formula:

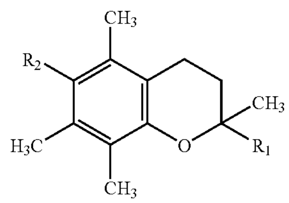

wherein $R_1$ is selected from the group consisting of a) H;

b) COOH; and c) $[CH_2CH_2CH_2(CH_3)]_3$—$CH_3$;

wherein $R_2$ is selected from the group consisting of a) H;

b) OH; and c) OAc; and wherein the isolated genomic DNA is in a solution containing bisulfite and a denaturing agent or is denatured in a solution containing bisulfite;

whereby the DNA is bisulfite converted.

2. The use according to claim 1, wherein the concentration of the compound is between 35 and 50 mmol/l.

3. The use according to claim 1, wherein the DNA is derived from body fluid.

4. The use according to claim 1, wherein the body fluid is serum or plasma.

5. The use according to claim 1, wherein the DNA is derived from tissue, sputum, stool, urine, or cerebrospinal fluid.

6. The use according to claim 1, further comprising analyzing the converted DNA by amplification of the DNA by a method selected from the group consisting of:

a) a method using methylation-specific blockers;

b) a method using methylation-sensitive PCR;

c) a method using primer extension reactions;

d) a method using hybridization of oligomer arrays; and e) a method using real time PCR.

7. The use according to claim 1, wherein the compound is 6-hydroxy-2,5,7,8-tetramethylchroman-2-carboxylic acid.

8. Use of a compound for the bisulfite conversion of DNA, said use comprising converting isolated genomic DNA in the presence of the compound, wherein the compound has the following formula:

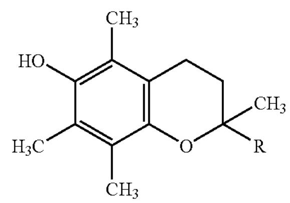

wherein R is selected from the group consisting of a) H;

b) COOH; and c) $[CH_2CH_2CH_2(CH_3)]_3$—$CH_3$; and wherein the isolated genomic DNA is in a solution containing bisulfite and a denaturing agent or is denatured in a solution containing bisulfite;

whereby the DNA is bisulfite converted.

9. The use according to claim 8, wherein the concentration of the compound is between 35 and 50 mmol/l.

10. The use according to claim 8, wherein the DNA is derived from body fluid.

11. The use according to claim 8, wherein the body fluid is serum or plasma.

12. The use according to claim 8, wherein the DNA is derived from tissue, sputum, stool, urine, or cerebrospinal fluid.

13. The use according to claim 8, comprising analyzing the converted DNA by amplification of the DNA by a method selected from the group consisting of:

a) a method using methylation-specific blockers;

b) a method using methylation-sensitive PCR;

c) a method using primer extension reactions;

d) a method using hybridization of oligomer arrays; and e) a method using real time PCR.

14. Use of a compound for the bisulfite conversion of DNA, said use comprising converting isolated genomic DNA in the presence of the compound, wherein the compound has the following formula:

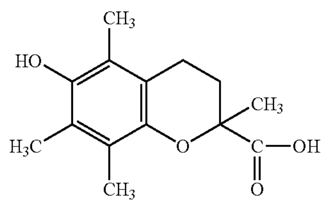

wherein the isolated genomic DNA is in a solution containing bisulfite and a denaturing agent or is denatured in a solution containing bisulfite;

whereby the DNA is bisulfite converted.

15. The use according to claim 14, wherein the concentration of the compound is between 35 and 50 mmol/l.

16. The use according to claim 14, wherein the DNA is derived from body fluid.

17. The use according to claim 14, wherein the body fluid is serum or plasma.

18. The use according to claim 14, wherein the DNA is derived from tissue, sputum, stool, urine, or cerebrospinal fluid.

19. The use according to claim 14, comprising analyzing the converted DNA by amplification of the DNA by a method selected from the group consisting of:

a) a method using methylation-specific blockers;
b) a method using methylation-sensitive PCR;
c) a method using primer extension reactions;
d) a method using hybridization of oligomer arrays; and
e) a method using real time PCR.

20. A method for the bisulfite conversion of DNA, wherein the method is conducted in the presence of a radical scavenger having the following formula:

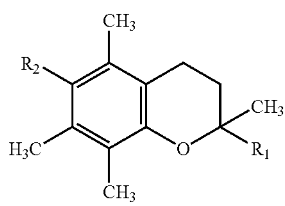

wherein $R_1$ is selected from the group consisting of
a) H;
b) COOH; and
C) $[CH_2CH_2CH_2(CH_3)]_3$—$CH_3$;
wherein $R_2$ is selected from the group consisting of
a) H;
b) OH; and
c) OAc; and
wherein the DNA is isolated genomic DNA in a solution containing bisulfite and a denaturing agent or is denatured in a solution containing bisulfite;
whereby the DNA is bisulfite converted.

21. The method according to claim 20, further comprising analyzing the converted DNA by amplification of the DNA by a method selected from the group consisting of:

a) a method using methylation-specific blockers;
b) a method using methylation-sensitive PCR;
c) a method using primer extension reactions;
d) a method using hybridization of oligomer arrays; and
e) a method using real time PCR.

22. The method according to claim 20, wherein the compound is 6-hydroxy-2,5,7,8-tetramethylchroman-2-carboxylic acid.

23. The method according to claim 20, wherein the bisulfite conversion is conducted at greater than 50° C. for greater than or equal to 5 hours.

24. The method according to claim 20, wherein the bisulfite conversion is conducted at a temperature of >55° C.

25. The method according to claim 20, wherein the bisulfite conversion is conducted at a temperature of 60° C. for 5 hours or at a temperature of 55° C. for 7 hours.

26. The method according to claim 20, wherein the DNA is derived from bodily fluid.

27. The method according to claim 26, wherein the bodily fluid is blood or plasma.

28. The method according to claim 20, wherein the bisulfite conversion is carried out in the presence of dioxane, a dioxane derivative, or a similar aliphatic cyclic ether.

29. The method according to claim 20, wherein the bisulfite conversion is carried out in the absence of denaturing solvents or reagents.

30. The method according to claim 20, wherein the reaction temperature is increased to a range of between 85° C. and 100° C. briefly during the course of the conversion.

31. The method according to claim 20, wherein the converted DNA is purified by a means of ultrafiltration.

32. A method for the bisulfite conversion of DNA, wherein the method is conducted in the presence of a radical scavenger having the following formula:

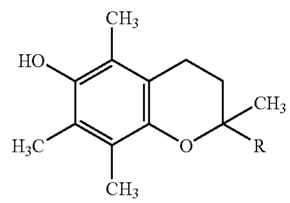

wherein R is selected from the group consisting of
a) H;
b) COOH; and
c) $[CH_2CH_2CH_2(CH_3)]_3$—$CH_3$; and
wherein the isolated genomic DNA is in a solution containing bisulfite and a denaturing agent or is denatured in a solution containing bisulfite;
whereby the DNA is bisulfite converted.

33. The method according to claim 32, further comprising analyzing the converted DNA by amplification of the DNA by a method selected from the group consisting of:

a) a method using methylation-specific blockers;
b) a method using methylation-sensitive PCR;
c) a method using primer extension reactions;
d) a method using hybridization of oligomer arrays; and
e) a method using real time PCR.

34. The method according to claim 32, wherein the bisulfite conversion is conducted at greater than 50° C. for greater than or equal to 5 hours.

35. A method for the bisulfite conversion of DNA, wherein the method is conducted in the presence of a radical scavenger having the following formula:

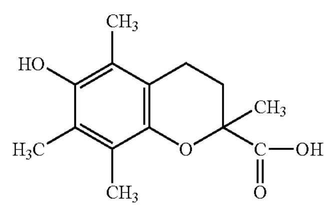

wherein the isolated genomic DNA is in a solution containing bisulfite and a denaturing agent or is denatured in a solution containing bisulfite;
whereby the DNA is bisulfite converted.

36. The method according to claim 35, further comprising analyzing the converted DNA by amplification of the DNA by a method selected from the group consisting of:

a) a method using methylation-specific blockers;

b) a method using methylation-sensitive PCR;

c) a method using primer extension reactions;

d) a method using hybridization of oligomer arrays; and e) a method using real time PCR.

37. The method according to claim 35, wherein the bisulfite conversion is conducted at greater than 50° C. for greater than or equal to 5 hours.

* * * * *